United States Patent [19]

Johnston

[11] B 4,001,234
[45] Jan. 4, 1977

[54] SUBSTITUTED PYRIMIDINYLOXY(THIO)PHENYL UREAS AND DERIVATIVES THEREOF

[75] Inventor: Howard Johnston, Walnut Creek, Calif.

[73] Assignee: The Dow Chemical Company, Midland, Mich.

[22] Filed: Jan. 22, 1974

[21] Appl. No.: 435,617

[44] Published under the second Trial Voluntary Protest Program on March 16, 1976 as document No. B 435,617.

[52] U.S. Cl. .................. 260/256.4 C; 260/256.4 N; 260/256.5 R; 424/251

[51] Int. Cl.$^2$ ..................................... C07D 239/34
[58] Field of Search ............ 260/256.4 C, 256.5 R, 260/256.4 N

*Primary Examiner*—Richard J. Gallagher
*Assistant Examiner*—James H. Turnipseed
*Attorney, Agent, or Firm*—S. Preston Jones; Gary D. Street; C. Kenneth Bjork

[57] ABSTRACT

Disclosed are novel substituted pyrimidinyloxy-(thio)-phenyl ureas and derivatives thereof. The compounds of the instant invention are useful as herbicides and can be formulated to provide herbicidal compositions.

16 Claims, No Drawings

SUBSTITUTED PYRIMIDINYLOXY(THIO)PHENYL UREAS AND DERIVATIVES THEREOF

SUMMARY OF THE INVENTION

The present invention is directed to substituted pyrimidinyloxy(thio)phenyl urea and derivatives thereof corresponding to the formula:

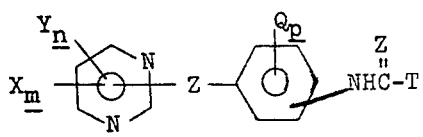

wherein:

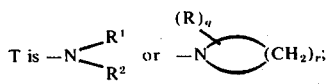

$r$ represents an integer of 4 or 5;
$q$ represents an integer of 0 to 2, inclusive;
$p$ represents an integer of 0 or 1;
each X independently represents bromo, chloro, iodo or fluoro;
$m$ represents an integer of 0 to 3, inclusive;
each Y independently represents cyano, nitro, $ZR^3$, $-C(X')_3$ or

$n$ represents an integer of 0 to 2, inclusive, the sum of $m + n$ being from 0 to 3, inclusive;
each Z independently represents oxygen or sulfur;
Q represents methyl, ethyl, halo, nitro, cyano or trifluoromethyl;
each X' independently represents hydrogen or halo;
each R independently represents hydrogen or an alkyl group of from about 1 to about 3 carbon atoms;
$R^1$ represents hydrogen, an alkyl group of from about 1 to about 4 carbon atoms or an alkoxy group of from about 1 to about 4 carbon atoms;
$R^2$ represents an alkyl group of from about 1 to about 3 carbon atoms or

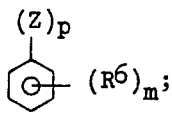

$R^3$ represents an alkyl group of from about 1 to about 3 carbon atoms;
$R^4$ and $R^5$ each independently represent hydrogen or an alkyl group of from about 1 to about 4 carbon atoms; and
each $R^6$ represents halo or an alkyl group of from about 1 to about 3 carbon atoms.

For the sake of brevity and simplicity, the term "active ingredient" is used hereinafter in this specification to broadly describe the compounds of the present invention. In the reaction sequences set forth below, all substituents, unless otherwise expressly indicated, are the same as set forth above.

The active ingredients of the present invention are normally crystalline solids and are soluble in the usual organic solvents, as well as having some solubility in water. The active ingredients are useful as plant growth regulants, and especially as herbicides when applied either as a pre-emergence or post-emergence treatment and may be formulated with the usual herbicide carriers for use in controlling unwanted plants.

DETAILED DESCRIPTION

The active ingredients of the present invention are useful as herbicides and certain of the active ingredients of the present invention have been found suitable in pre- and post-emergence applications for controlling unwanted plants among crops such as, for example, corn, wheat, soybeans, cotton or rice, without injuring the crops. As used in the present specification and claims, the term "herbicide" means an active ingredient which, when used in a growth controlling amount, controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant germinant seeds, emerging seedlings, and established vegetation, including the roots and above-ground portions.

The term "alkyl" is used herein and in the appended claims to designate a straight or branched chain alkyl radical containing from 1 to about 4 carbon atoms, such as, for example, methyl, ethyl, propyl, isopropyl, butyl, isobutyl and tert-butyl. The term "alkoxy" as employed designates a straight or a branched-chain radical containing from 1 to about 4 carbon atoms, such as, for example, methoxy, ethoxy, propoxy, isopropoxy, butoxy, isobutoxy and tert-butoxy.

The terms "halo" and "halogen" are employed herein to represent chlorine, fluorine and bromine.

Preferred compounds of the present invention are those compounds wherein $n$ is 0 and $m$ is at least 1. In a further preferred embodiment, $m$ is 0 and $n$ is at least 1. In another embodiment, those compounds wherein the sum of $m + n$ is at least two are preferred. Another class of preferred compounds includes those wherein T is $-NR^1R^2$. A further class of preferred compounds includes those wherein T is $-NR^1R^2$ and $R^1$ and $R^2$ each represent alkyl. Still another preferred class of compounds includes those wherein T is $-NR^1R^2$, $R^1$ is alkoxy and $R^2$ is alkyl. In still another preferred embodiment,

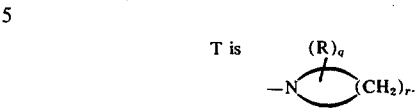

The active ingredients of the present invention wherein T is $-NR^1R^2$ and wherein $R^1$ and $R^2$ is hydrogen or alkyl, conveniently hereinafter referred to as "pyrimidinyl urea" compounds, can readily be prepared by reacting a selected substituted halopyrimidine reactant with a salt of a selected substituted urea(thio)phenol reactant as illustrated in the following representative reaction sequence:

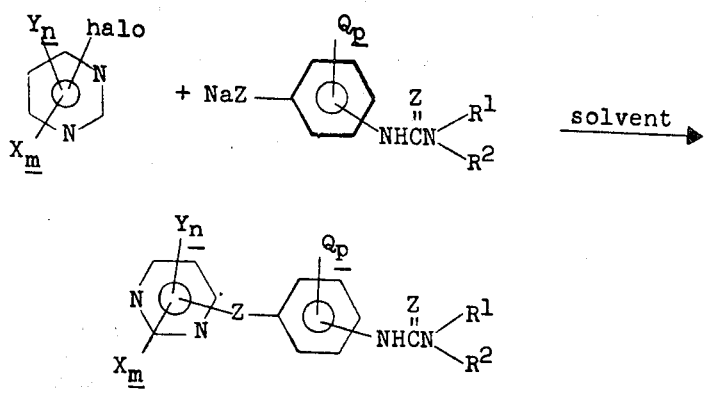

Reaction I

The reaction proceeds readily under ambient atmospheric pressure and at temperatures of from about 50° to about 100°C. In carrying out the reaction a solution of the sodium urea(thio)phenate reactant in methanol is added, ordinarily portionwise, to a solution of the substituted halopyrimidine reactant in an inert solvent carrier such as, for example, dimethylsulfoxide, n-formylmorpholine or the like. Stoichiometric proportions of the reactants are usually employed.

The substituted urea(thio)phenate solution is prepared by rapidly adding stoichiometric proportions of the substituted urea(thio)phenol reactant to a solution of sodium metal in methanol. The sodium urea(thio)phenate solution is usually mixed with the halopyrimidine reactant in a solvent carrier. The resulting reaction mixture is maintained at temperatures between about 50° and 100°C., preferably between about 60° and 90°C., for a period of from about 1 to about 3 hours. Following the substantial completion of the reaction, the reaction mixture is cooled to about 50°C., mixed with ice water and the resulting precipitate recovered by filtration, washed with water and dried. The reaction product thus obtained can be employed as is or further purified by recrystallization from a solvent or solvent mixture such as, for example, acetonitrile, methylene chloride or the like.

The substituted urea(thio)phenol reactants are readily prepared by reacting a selected substituted amino-(thio)phenol reactant with a selected substituted carbamoyl halide reactant in the presence of an inert solvent carrier, such as pyridine or the like. Stoichiometric proportions of the reactants are usually employed and the reaction is ordinarily carried out at ambient temperatures and pressure conditions over a period of from about 10 to about 25 hours. Following the substantial completion of the reaction, the desired urea(thio)phenol reactant is obtained in procedures analogous to those set forth hereinbefore.

In alternative procedures, the pyrimidinyl urea compounds of the present invention can likewise be prepared by first preparing selected substituted pyrimidinyl nitrobenzene reactant, converting the same to a corresponding pyrimidinylbenzenamine, which is subsequently reacted with a selected substituted carbamoyl halide reactant. Such reaction sequence is illustrated as follows:

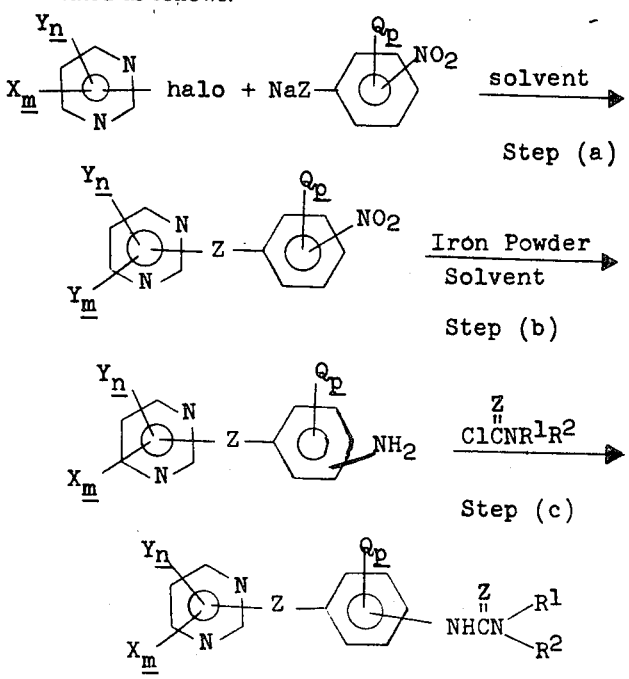

Reaction II

The reaction in step (a) above proceeds readily under ambient atmospheric pressure at reaction temperatures of from about 100° to about 160°C. for a period of from about 3 to about 5 hours. In such operations, the salt of the substituted nitrophenol or nitrothiophenol is mixed with the selected halopyrimidine reactant in the presence of an inert solvent, such as previously mentioned with respect to Reaction I, and the resulting reaction mixture heated at a temperature within the above indicated ranges. Following the substantial completion of the reaction, the reaction mixture is cooled and mixed with cold water. The resulting product precipitate is recovered by filtration and recrystallized according to conventional techniques from a solvent such as previously mentioned.

The product thus obtained from step (a) of Reaction II is mixed, in the presence of an aqueous alcohol solution, with a reducing agent, such as, for example, iron powder. The resulting reaction mixture is heated to the reflux temperature thereof with vigorous stirring and an alcohol solution of concentrated hydrochloric acid is added thereto, portionwise, over a 10 to 30 minute period. The reaction mixture is heated at the reflux temperature for a period of from about 2 to about 4 hours and filtered while hot. The solid product thus obtained is washed with an aqueous alkanol solution, such as 50–95% ethanol, and the filtrate portions combined and extracted with a solvent such as benzene, methylene chloride or the like. The extract is then dried, treated with activated charcoal, such as Norite, filtered and evaporated to dryness to obtain the desired pyrimidinylbenzenamine reactant which is then reacted with a selected carbamoyl halide reactant according to the procedures set forth above with respect to the preparation of the urea(thio)phenol reactants.

The pyrrolidine- and piperidine- carboxamide derivatives of the present invention, i.e., wherein T is

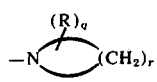

are prepared by reacting the amine intermediates of the present invention (prepared in step (b) of Reaction II) with phosgene or thiophosgene in the presence of toluene to form a corresponding novel pyrimidinyloxy(thio)phenyl iso- or isothio- cyanate intermediate, hereinafter referred to as "isocyanate" intermediates, which can then be reacted with a selected pyrrolidine or piperidine reactant to obtain the desired product. The essential steps of the reaction sequence can be schematically illustrated as follows:

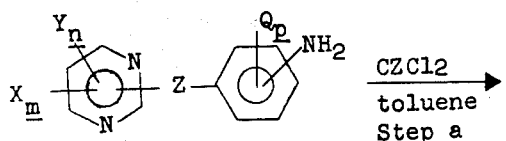

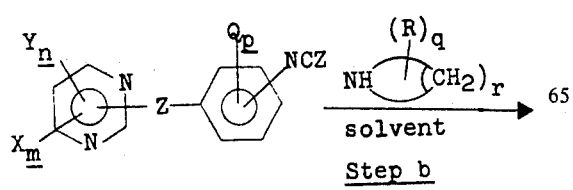

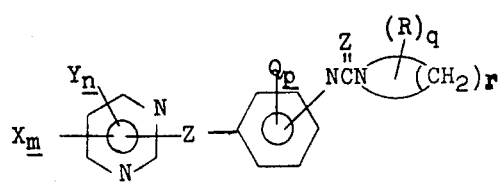

Reaction III

The isocyanate intermediates are readily prepared according to step (a) above by first preparing a solution of phosgene or thiophosgene in a solvent such as, for example, water, toluene or the like, and then rapidly adding, with stirring, a solution of the benzenamine starting material in toluene. The benzenamine addition is regulated so as to maintain the temperature of the mixture at about 5°C. or less, with additional quantities of solvent being added if necessary. Following the completion of the benzenamine addition, the reaction mixture is agitated and heated gradually until a temperature of from about 70° to about 100°C. is reached. The solvent carrier is then removed from the reaction mixture by evaporation under reduced pressure and the remaining residue taken up in hexane which is then cooled to crystallize the desired product. An excess of phosgene or thiophosgene, in a ratio of from about 3 to about 4 moles thereof per mole of benzenamine reactant, is preferably employed in the reaction. During the reaction, excess phosgene can be removed by purging the reaction mixture with an inert gas, such as nitrogen.

In step (b) of Reaction IV, the isocyanate intermediate is reacted with the selected pyrrolidine or piperidine reactant under reaction conditions generally the same as for the hereinbefore described procedures in step (c) of Reaction II. Stoichiometric quantities of the reactants are usually employed.

The isocyanate intermediates prepared in step (a) of Reaction IV are also employed in the preparation of compounds of the instant invention wherein

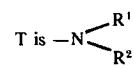

and $R^1$ is alkoxy and $R^2$ is alkyl. Other pyrimidinyl urea compounds of the present invention can also be prepared from the isocyanate intermediates. In such operations, the isocyanate intermediates are reacted with an appropriately substituted hydroxyl amine salt reactant in the presence of an inert solvent, such as, for example, pyridine according to the following illustrative reaction sequence:

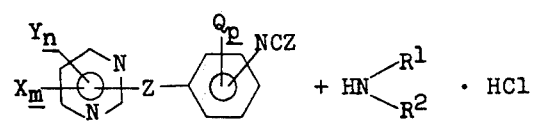

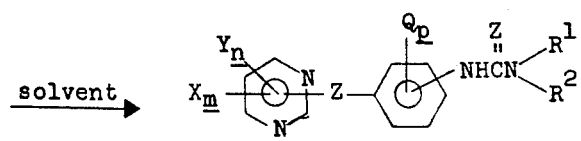

Reaction IV

The reaction is conducted under ambient atmospheric pressure at temperatures of from about 50° to about 100°C. Preferably, an actuating agent is employed to increase the reaction rate. Representative actuating agents that can be employed include, for example, tertiary amines such as triethylamine and the like. The reactants are usually employed in stoichiometric proportions while an excess of the actuating agent is employed.

In carrying out the reaction, the isocyanate and substituted hydroxylamine reactants are contacted in the presence of a dry inert solvent containing the actuating agent. Representative solvents include, for example, pyridine, toluene or the like. The resulting reaction mixture is heated with stirring at a temperature within the above described range for a period of from about ½ to about 2 or more hours. The reaction mixture is then stirred at ambient temperatures for a period of from about 1 to about 12 hours and then cooled and mixed with cold water. The resulting product precipitate is recovered and purified in typical procedures previously set forth.

The following examples illustrate the present invention and the manner by which it can be practiced but, as such, should not be construed as limitations upon the overall scope of the same.

EXAMPLE 1

N'-(4-((2-chloro-4-pyrimidinyl)oxy)phenyl)-N,N-dimethylurea

4-Hydroxyphenyl-N,N-dimethylurea (12.0 grams; 0.066 mole) was mixed with a solution of sodium methylate (prepared by mixing sodium metal (1.53 grams) in 55 milliliters (ml) of methanol) and the resulting sodium 4-hydroxyphenyl-N,N-dimethylurea solution added gradually over a period of about one hour to a solution of 2,4-dichloropyrimidine (9.94 grams; 0.066 mole) in 50 ml. of dimethylsulfoxide. During the addition, the reaction temperature rose from about 55°C. to a temperature from between about 60° to about 65°C. The resulting reaction mixture was maintained at temperatures from between about 60° to about 70°C. for a period of about 30 minutes. The reaction mixture, which was nearly neutral, was poured into about 300 ml. of cold water and the resulting product precipitate recovered by filtration and washed with additional portions of water. The product precipitate was dissolved in acetonitrile and the resulting solution filtered with activated charcoal and then cooled to crystallize the product. The product thus obtained was recrystallized again from methylene chloride and dried. As a result of these operations, the desired title product was obtained as a white solid having a melting point of 192°C.

EXAMPLE 2

N'-(4-((2-chloro-6-methyl-4-pyrimidinyl)oxy)-phenyl)-N,N-dimethylurea

4-Hydroxyphenyl-N,n-dimethylurea (14.4 grams; 0.08 mole) was mixed with a solution of sodium methylate (prepared by mixing sodium metal (1.84 grams) in 50 milliliters (ml) of methanol) and the resulting sodium 4-hydroxyphenyl-N,N-dimethylurea solution added gradually over a period of about one hour to a solution of 2,4-dichloro-6-methylpyrimidine (13.04 grams; 0.08 mole) in 70 ml. of dimethylsulfoxide. During the addition, the reaction temperature rose from about 52°C. to a temperature from between about 60° to about 65°C. The resulting reaction mixture was maintained at temperatures from between about 60° to about 70°C. for a period of about 80 minutes. Following the reaction period, the reaction mixture was poured into about 400 ml. of cold water and the resulting tan product precipitate recovered by filtration and washed with additional portions of water. The product precipitate was dissolved in boiling benzene and the resulting solution treated with activated charcoal. Approximately one-half of the solvent was removed by evaporation and the remaining portion was cooled to crystallize the product. As a result of these operations, the desired title product was obtained as a light tan crystalline solid having a melting point of 176°–178°C.

Other urea compounds and derivatives are similarly prepared from selected substituted amine or isocyanate intermediates in accordance with the procedures of the foregoing Examples and the foregoing teachings of the specification. Such other compounds include, inter alia, the following:

N'-(4-((2,5,6-trichloro-4-pyrimidinyl)oxy)phenyl)-N,N-dimethylurea;

N'-(4-((2-methoxy-4-pyrimidinyl)oxy)phenyl)-N,N-dimethylurea;

N-butyl-N'-(4-((2-fluoro-4-pyrimidinyl)oxy)phenyl)-N-methylurea;

N'-(4-((2-bromo-4-pyrimidinyl)oxy)phenyl)-N-methyl-N-methoxyurea;

N'-(4-((2-iodo-4-pyrimidinyl)thio)-3-chlorophenyl)-N-methyl-N-butoxyurea;

N-butoxy-N-propyl-N'-(4-((2,5,6-trichloro-4-pyrimidinyl)oxy)-3-methylphenyl)urea;

N-(4-((2,5,6-tribromo-4-pyrimidinyl)thio)-3-cyanophenyl)-1-pyrrolidinecarboxamide;

N-(4-((2-(trifluoromethyl)-4-pyrimidinyl)thio)-3-nitrophenyl)-1-piperidinecarboxamide;

N-(4-((2-chloro-6-(trifluoromethyl)-4-pyrimidinyl)-oxy)-3-(trifluoromethyl)phenyl)-2,5-dimethyl-1-pyrrolidinecarboxamide;

N-((4-chlorophenyl)thio)-N'-(4-((2-chloro-4-pyrimidinyl)oxy)phenyl)-N-methylurea;

N'-((4-(6-cyano-4-pyrimidinyl)thio)phenyl)-N,N-dimethylurea;

N'-(4-((2,5-dichloro-6-fluoro-4-pyrimidinyl)oxy)-phenyl)-N,N-dimethylurea;

N'-(4-((2,5-bis(trifluoromethyl)-4-pyrimidinyloxy)-phenyl)-N,N-dimethylthiourea;

N'-((3-(5-chloro-4-pyrimidinyl)thio)phenyl)-N,N-dimethylthiourea;
N,N-dimethyl-N'-(4-(5-pyrimidinyloxy)phenyl)urea;
N,N-dimethyl-N'-(4-((2-nitro-5-pyrimidinyl)oxy)phenyl)urea;
N,N-dimethyl-N'-(4-((2-(methylthio)-4-pyrimidinyl)oxy)phenyl)urea;
N'-(4-((2-chloro-4-pyrimidinyl)oxy)phenyl)-N,N-dimethylurea;
N'-(4-((2,5-dichloro-4-pyrimidinyl)oxy)phenyl)-N,N-dimethylthiourea;
N,N-dimethyl-N'-(4-((2-methyl-5-pyrimidinyl)oxy)phenyl)urea;
N'-(4-((2-chloro-5-cyano-2-pyrimidinyl)thio)phenyl)-N,N-dimethylurea;
N'-(4-((5-chloro-2-cyano-4-pyrimidinyl)oxy)phenyl)-N,N-dimethylurea;
N'-(4-((2-chloro-5-(trifluoromethyl)-4-pyrimidinyl)oxy)phenyl)-N-methyl-N-methylurea;
N-methoxy-N-methyl-N'-(4-(((2-trifluoromethyl)-2-pyrimidinyl)oxy)phenyl)thiourea;
N'-(4-((4-cyano-5-pyrimidinyl)oxy)phenyl)-N,N-dimethylurea;
N,N-dimethyl-N'-(4-((2-(propylthio)-4-pyrimidinyl)oxy)phenyl)urea;
N'-(4-((2-chloro-4-pyrimidinyl)oxy)-3-(trifluoromethyl)phenyl)-N,N-dimethylurea;
N,N-dimethyl-N'-(4-((2-propoxy)-5-pyrimidinyl)oxy)phenyl)urea;
N-(4-((2-chloro-4-pyrimidinyl)oxy)phenyl)-2,5-dimethyl-1-pyrrolidinecarboxamide;
N,N-dimethyl-N'-(4-(4-methyl-5-pyrimidinyl)oxy)phenyl)thiourea;
N'-(4-((2-chloro-5-(chlorodifluoromethyl)-4-pyrimidinyl)oxy)phenyl)-N,N-dimethylurea;
N-((3,4,5-tribromophenyl)thio)-N'-(3-((2-chloro-6-amino-4-pyrimidinyl)oxy)phenyl)-N-methylurea;
N'-(3-((2,6-dicyano-4-pyrimidinyl)oxy)-4-ethylphenyl)-N-methoxy-N-methylurea;
N'-(4-((6-(trifluoromethyl)-4-pyrimidinyl)thio)-3-cyanophenyl)-N,N-ethylurea;
N'-(5-((2-bromo-6-methylamino-4-pyrimidinyl)thio)-3-bromophenyl)-N-butyl-N-methylthiourea;
N-butoxy-N'-(3-((5-(dichloromethyl)-4-pyrimidinyl)oxy)-4-cyanophenyl)-N-propylurea;
N'-(4-((2-methyl-5,6-dichloro-4-pyrimidinyl)thio)-3-methylphenyl)-N,N-dimethylurea;
N'-(4-((2,5-dimethyl-6-chloro-4-pyrimidinyl)oxy)-3-fluorophenyl)-N-methyl-N-methoxythiourea;
N-(4-((2,6-dinitro-4-pyrimidinyl)oxy)phenyl)-3-propyl-1-piperidinecarboxamide;
N-(4-((5-chloro-2,6-dimethoxy-4-pyrimidinyl)oxy)-3-chlorophenyl)-2,6-dimethyl-1-piperidinethiocarboxamide;
N'-(5-((6-bromo-2-n-butylamino-4-pyrimidinyl)-thio)-3-(trifluoromethyl)phenyl)-N-ethoxy-N-methylthiourea;
N'-(3-((2-di-n-butylamino-5-methyl-4-pyrimidinyl)oxy)phenyl)-N,N-dimethylurea;
N-(4-((5,6-dichloro-2-cyano-4-pyrimidinyl)-thio)-2-chlorophenyl)-1-pyrrolidinecarboxamide;
N'-(4-((2,6-diamino-5-chloro-4-pyrimidinyl)oxy)-phenyl)-N,N-dimethylurea;
N'-(5-((6-chloro-2,5-dinitro-4-pyrimidinyl)thio)-3-methylphenyl)-N,N-di-n-propylurea;
N-((3,5-di-i-propylphenyl)oxy)-N'-(4-((2,6-bis-(trifluoromethyl)-4-pyrimidinyl)oxy)-N-methylthiourea;

N'-(4-((5,6-dichloro-2-(difluoromethyl)-4-pyrimidinyl)oxy)phenyl)-N,N-dimethylurea;
N'-(4-((2,6-di-(dimethylamino)-4-pyrimidinyl)thio)-phenyl)-N-methoxy-N-methylthiourea;
N'-(4-((2-cyano-6-(trifluoromethyl)-4-pyrimidinyl)-thio)phenyl)-N,N-dimethylthiourea;
N'-(4-((2-methyl-6-(trifluoromethyl)-4-pyrimidinyl)-thio)phenyl)-1-piperidinecarboxamide;
N-(4-((5-methyl-6-nitro-4-pyrimidinyl)oxy)-3-chlorophenyl)-1-pyrrolidinecarboxamide;
N'-(4-((2-cyano-6-nitro-4-pyrimidinyl)thio)phenyl)-N-methoxy-N-methylurea;
N'-(4-((6-cyano-2-methylamino-4-pyrimidinyl)oxy)-phenyl)-N,N-dimethylthiourea;
N'-(4-((2-nitro-4-(trifluoromethyl)-4-pyrimidinyl)-oxy)phenyl)-N-methoxy-N-methylurea;
N'-(4-((6-amino-5-trifluoromethyl-4-pyrimidinyl)-thio)-3-methylphenyl)-N,N-dimethylthiourea and
N'-(3-((2-propylthio-6-(trifluoromethyl)-4-pyrimidinyl)oxy)phenyl)-N,N-dimethylurea.

The amine and isocyanate intermediates are readily apparent in view of the foregoing enumerated compounds. Such amine intermediates employed in alternative methods of preparing the pyrimidinyl urea compounds are of the formula represented in Reaction Sequences II and III of the specification and are prepared in accordance withe the teachings of the specification. The nomenclature for such amine intermediates, for example, the corresponding amine intermediate to the compound of Example 1, would be N'-(4-((2-chloro-4-pyrimidinyl)oxy)phenyl)-benzenamine.

The isocyanate intermediates employed to prepare the pyrimidinyl carboxamide compounds as well as other of the above-enumerated compounds are likewise readily apparent in view of the foregoing compounds. Such isocyanate intermediates correspond to the general formula represented in reactions III and IV set forth hereinbefore and are prepared according to the teachings set forth in the specification. The isocyanate compound employed for the preparation of the compound of Example 1, or other carboxamide compounds, would be N'-(4-((2-chloro-4-pyrimidinyl)oxy)phenyl)isocyanate. Other amine and isocyanate intermediates are similarly prepared and named.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of a herbicidally-effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, keiselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propyl-naphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (non-ionic 218), long chain ethylene oxidepropylene oxide condensation products, e.g., Pluronic 61 (molecular weight 1000), polyethylene glycol ester of tall oil acids, sodium octyl phenoxyethoxyethyl sulfate, tris(polyoxyethylene) sorbitan monostearate (Tween 60), and sodium dihexyl sulfosuccinate.

The concentration of the active ingredients in liquid compositions generally is from about 0.003 to about 95 percent by weight or more. Concentrations of from about 0.003 to about 50 weight percent are often employed. In dusts or dry formulations, the concentration of the active ingredient can be from about 0.003 to about 95 weight percent or more; concentrations of from about 0.003 to about 50 weight percent are often conveniently employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of powder-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments the compositions of this invention are usually applied at an approximate rate of from about 1 to about 25 lbs. per acre, but lower or higher rates may be appropriate in some cases. In selective post-emergence operations to foliage, a dosage of from about 0.08 to about 5.0 pounds per acre is usually employed. In some instances, lower dosages may be utilized while higher dosages may be necessary in other instances. In view of the foregoing and following disclosures, one skilled in the art can readily determine the optimum rate to be applied in any particular case.

So as to illustrate the general and selective phytotoxic properties of the active ingredients of the present invention, a group of controlled greenhouse experiments is described below.

In pre-emergence operations, seeds of selected species are planted in seedbeds and, while exposed, sprayed with a given volume of a solution containing a predetermined amount of the candidate active ingredient to provide the dosage rate desired. Such compositions are prepared by mixing the selected active ingredient and an emulsifier or dispersant with water. The seeds are then covered with a layer of soil and maintained under conditions conducive to growth. A portion of the planted seedbeds are left untreated to provide controls for comparative purposes. All seedbeds are watered from below as needed. About 14 days after seeding and treating, the effect of each of the test ingredients on the seeds is evaluated by a comparison with the control seedbeds.

In post-emergence operations, various species of plants are seeded in beds of good agricultural soil. After the plants have emerged and grown to a height of from about 2 to 6 inches, certain of the plants are sprayed to run-off with a given volume of a composition prepared as set forth above. Other plants are left untreated to provide comparative controls. All plants are maintained as above for a period of about 14 days and then evaluated to determine the effect of each test ingredient.

In representative general pre-emergence operations, each of the N'-(4-((2-chloro-6-methyl-4-pyrimidinyl)oxy)phenyl)-N,N-dimethylurea and N'-(4-((2-chloro--4-pyrimidinyl)oxy)phenyl)-N,N-dimethylurea compounds was found to give from substantial (at least 70%) to complete (100%) control of the growth of German millett, barnyard grass, crab grass, pigweed, velvet leaf and morning glory at dosage rates of 4 pounds per acre, respectively.

In representative selective pre-emergence operations, N'-(4-((2-chloro-6-methyl-4-pyrimidinyl)oxy)phenyl)--N,N-dimethylurea was found to give substantial to complete control of crabgrass, pigweed and velvet leaf at a dosage rate of one pound per acre without inhibiting the growth of cornseeds.

In additional representative post-emergence operations, each of the N'-(4-((2-chloro-6-methyl-4-pyrimidinyl)oxy)phenyl)-N,N-dimethylurea and N'-(4-((2-chloro-4-pyrimidinyl)oxy)phenyl)-N,N-dimethylurea compounds was found to give substantial to complete control of German millett, barnyard grass, crab grass, pigweed, velvet leaf and annual morning glory when such plants are contacted with sufficient amounts of compositions containing the active ingredients to provide a dosage rate of ten pounds per acre.

In representative selective post-emergence operations, the N'-(4-((2-chloro-4-pyrimidinyl)oxy)phenyl)-N,N-dimethylurea compound was found to give substantial to complete control of barnyard grass, crab grass, pigweed, bindweed, valvet leaf and annual morning glory at a dosage rate of 0.32 pounds per acre while having no effect on corn, rice, wheat, soybean and cotton plants at such dosage.

The substituted halopyrimidine, urea(thio)phenol, nitro(thio)phenol, carbamoyl halide, hydroxyl amine, pyrrolidine and piperidine reactants which can be employed to prepare the compounds of the present invention are either readily available or can be prepared according to procedures which are known or are analogous to those set forth in the open literature.

Although the invention is described with respect to specific embodiments and modifications, the details thereof are not to be construed as limitations except to the extent indicated in the following claims.

I claim:
1. A compound corresponding to the formula:

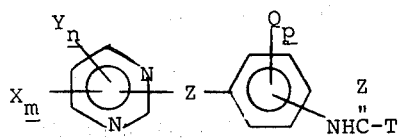

wherein:

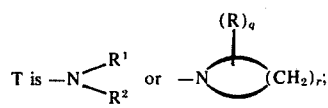

$r$ represents an integer of 4 or 5;
$q$ represents an integer of 0 to 2, inclusive;
$p$ represents an integer of 0 or 1;
each X independently represents bromo, chloro, iodo or fluoro;
$m$ represents an integer of 0 to 3, inclusive;
each Y independently represents cyano, nitro, $ZR^3$, $-C(X')_3$ or

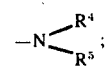

$n$ represents an integer of 0 to 2, inclusive, the sum of $m + n$ being from 0 to 3, inclusive;
each Z independently represents oxygen or sulfur;
Q represents methyl, ethyl, halo, nitro, cyano or trifluoromethyl;
each $X'$ independently represents hydrogen or halo;
each R independently represents hydrogen or alkyl of from 1 to 3 carbon atoms;
$R^1$ represents hydrogen, alkyl of from 1 to 4 carbon atoms or alkoxy of from 1 to 4 carbon atoms;
$R^2$ represents alkyl of from 1 to 3 carbon atoms or

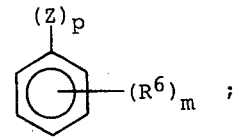

$R^3$ represents alkyl of from 1 to 3 carbon atoms;
$R^4$ and $R^5$ each independently represent hydrogen or alkyl of from 1 to 4 carbon atoms; and
each $R^6$ represents halo or alkyl of from 1 to 3 carbon atoms.

2. The compound of claim 1 wherein $n$ is 0 and $m$ is at least one.
3. The compound of claim 1 wherein $m$ is 0 and $n$ is at least one.
4. The compound of claim 1 wherein the sum of $m + n$ is at least two.
5. The compound of claim 1 wherein

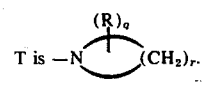

6. A compound of the formula:

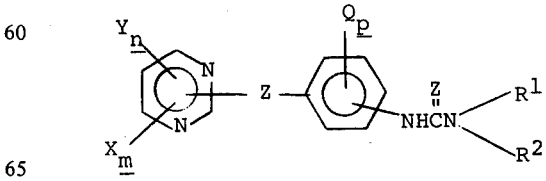

wherein:
each $p$ represents an integer of 0 or 1;

each X independently represents bromo, chloro, iodo or fluoro;
m represents an integer of 0 to 3, inclusive;
each Y independently represents cyano, nitro, $ZR^3$, —$C(X')_3$ or

n represents an integer of 0 to 2, inclusive, the sum of $m + n$ being from 0 to 3, inclusive;
each Z independently represents oxygen or sulfur;
Q represents methyl, ethyl, halo, nitro, cyano or trifluoromethyl;
each X' independently represents hydrogen or halo;
each R independently represents hydrogen or alkyl of from 1 to 3 carbon atoms;
$R^1$ represents hydrogen, alkyl of from 1 to 4 carbon atoms or alkoxy of from 1 to 4 carbon atoms;
$R^2$ represents alkyl of from 1 to 3 carbon atoms or

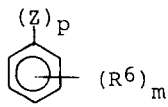

$R^3$ represents alkyl of from 1 to 3 carbon atoms;
$R^4$ and $R^5$ each independently represent hydrogen or alkyl of from 1 to 4 carbon atoms; and
each $R^6$ represents halo or alkyl of from 1 to 3 carbon atoms.

7. The compound of claim 6 wherein n is 0 and m is at least one.

8. The compound of claim 6 wherein m is 0 and n is at least one.

9. The compound of claim 6 wherein $R^1$ and $R^2$ represent alkyl.

10. The compound of claim 6 wherein $R^1$ is alkoxy and $R^2$ is alkyl.

11. The compound of claim 9 wherein n is 0 and m is at least one.

12. The compound of claim 10 wherein n is 0 and m is at least one.

13. The compound of claim 6 which is N'-(4-((2-chloro-4-pyrimidinyl)oxy)phenyl)-N,N-dimethylurea.

14. The compound of claim 6 which is N'-(4-((2-chloro-6-methyl-4-pyrimidinyl)oxy)phenyl)-N,N-dimethylurea.

15. A compound corresponding to the formula:

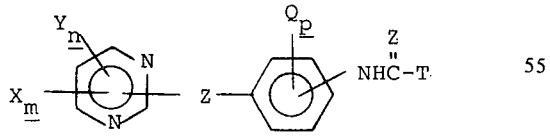

wherein:

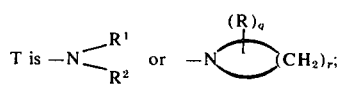

r represents an integer of 4 or 5;
q represents an integer of 0 to 2, inclusive;
p represents an integer of 0 or 1;

each X independently represents bromo, chloro, iodo or fluoro;
m represents an integer of 0 to 3, inclusive;
each Y independently represents cyano, nitro, $ZR^3$, —$C(X')_3$ or

n represents an integer of 0 to 2, inclusive, the sum of $m + n$ being from 0 to 3, inclusive;
Z represents oxygen;
Q represents methyl, ethyl, halo, nitro, cyano or trifluoromethyl;
each X' independently represents hydrogen or halo;
each R independently represents hydrogen or alkyl of from 1 to 3 carbon atoms;
$R^1$ represents hydrogen, alkyl of from 1 to 4 carbon atoms or alkoxy of from 1 to 4 carbon atoms;
$R^2$ represents alkyl of from 1 to 3 carbon atoms or

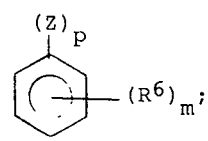

$R^3$ represents alkyl of from 1 to 3 carbon atoms;
$R^4$ and $R^5$ each independently represent hydrogen or alkyl of from 1 to 4 carbon atoms; and
each $R^6$ represents halo or alkyl of from 1 to 3 carbon atoms.

16. A compound of the formula:

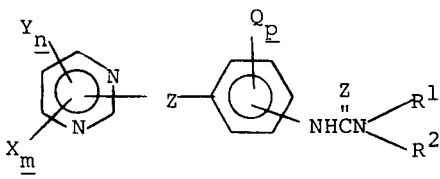

wherein:
each p represents an integer of 0 or 1;
each X independently represents bromo, chloro, iodo or fluoro;
m represents an integer of 0 to 3, inclusive;
each Y independently represents cyano, nitro, $ZR^3$, —$C(X')_3$ or

n represents an integer of 0 to 2, inclusive, the sum of $m + n$ being from 0 to 3, inclusive;
Z represents oxygen;
Q represents methyl, ethyl, halo, nitro, cyano or trifluoromethyl;
each X' independently represents hydrogen or halo;
each R independently represents hydrogen or alkyl of from 1 to 3 carbon atoms;
$R^1$ represents hydrogen, alkyl of from 1 to 4 carbon atoms or alkoxy of from 1 to 4 carbon atoms;
$R^2$ represents alkyl of from 1 to 3 carbon atoms or

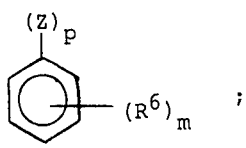
$R^3$ represents alkyl of from 1 to 3 carbon atoms;
$R^4$ and $R^5$ each independently represent hydrogen or alkyl of from 1 to 4 carbon atoms; and
each $R^6$ represents halo or alkyl of from 1 to 3 carbon atoms.
* * * * *